(12) United States Patent
Walker

(10) Patent No.: US 12,042,512 B2
(45) Date of Patent: Jul. 23, 2024

(54) METHOD AND USE OF COMPOSITIONS COMPRISING LIGNOSULFONATE AND SUBSTANTIALLY FREE OF ELEMENTAL SULPHUR FOR PATHOGENIC ATTENUATION

(71) Applicant: Attenubiotics Inc., Calgary (CA)

(72) Inventor: Ralph Kevin Walker, Calgary (CA)

(73) Assignee: Attenubiotics Inc., Calgary (CA)

( * ) Notice: Subject to any disclaimer, the term of this patent is extended or adjusted under 35 U.S.C. 154(b) by 0 days.

(21) Appl. No.: 16/523,901

(22) Filed: Jul. 26, 2019

(65) Prior Publication Data

US 2020/0054670 A1    Feb. 20, 2020

Related U.S. Application Data

(60) Provisional application No. 62/703,755, filed on Jul. 26, 2018.

(51) Int. Cl.
*A61K 31/795* (2006.01)
*A61K 9/00* (2006.01)
*A61P 3/10* (2006.01)

(52) U.S. Cl.
CPC .......... *A61K 31/795* (2013.01); *A61K 9/0056* (2013.01); *A61P 3/10* (2018.01)

(58) Field of Classification Search
CPC ...................................................... A61K 31/795
USPC ....................................................... 514/709
See application file for complete search history.

(56) References Cited

U.S. PATENT DOCUMENTS 4,185,097 A    1/1980 Ward et al.
2015/0132390 A1    5/2015 Walker

FOREIGN PATENT DOCUMENTS

WO    2007140588 A1    12/2007
WO    2012/094838 A1    7/2012

OTHER PUBLICATIONS

Material Safety Data Sheet, online <https://www.maritimehydroseed.com/images/TDS_MSDS.pdf>, Mar. 23, 2010, accessed Apr. 30, 2020.
Qui et al., Lignosulfonic acid exhibits broadly Anti-HIV-1 activity—potential as a microbiocide candidate for the prevention of HIV-1 sexual transmission, PloS One, Apr. 27, 2012, 7/4, e35906.
Fukuchi et al. Lignosulfonic rapidly inactivates human immunodeficiency and herpes simplex viruses, Medicines, Oct. 3, 2021, 8, 56.
Hasegawa, Yasushi et al. "Lignosulfonic Acid-Induced Inhibition of Intestinal Glucose Absorption." Journal of nutritional science and vitaminology vol. 61,6 (2015): 449-54. doi:10.3177/jnsv.61.449.
Hasegawa, Yasushi et al. "Lignosulfonic acid promotes hypertrophy in 3T3-L1 cells without increasing lipid content and increases their 2-deoxyglucose uptake." Asian-Australasian journal of animal sciences vol. 30,1 (2017): 111-118. doi: 10.5713/ajas.16.0253.
Barnard, D L, and K W Heaton. "Bile acids and vitamin A absorption in man: the effects of two bile acid-binding agents, cholestyramine and lignin." Gut vol. 14,4 (1973): 316-8. doi:10.1136/gut.14.4.316.
Zakzeski J, Bruijnincx PCA, Jongerius AL, Weckhuysen BM. The catalytic valorization of lignin for the production of renewable chemicals. Chem Rev. Jun. 9, 2010;110(6):3552-99.
Karlsson MG, Lawesson SS, Ludvigsson J. Th1-like dominance in high-risk first-degree relatives of type I diabetic patients. Diabetologia. Jun. 2000;43(6):742-9.
Halminen M, Simell O, Knip M, Ilonen J. Cytokine expression in unstimulated PBMC of children with type 1 diabetes and subjects positive for diabetes-associated autoantibodies. Scand J Immunol. May 2001;53(5):510-3.
Karlsson Faresjö MGE, Ernerudh J, Ludvigsson J. Cytokine profile in children during the first 3 months after the diagnosis of type 1 diabetes. Scand J Immunol. May 2004;59(5):5 17-26.
Stechova K, Bohmova K, Vrabelova Z, Sepa A, Stadlerova G, Zacharovova K, et al. High T-helper-1 cytokines but low T-helper-3 cytokines, inflammatory cytokines and chemokines in children with high risk of developing type 1 diabetes. Diabetes Metab Res Rev. Sep. 2007;23(6):462-71.
Myrvold BO. A new model for the structure of lignosulphonates. Part 1. Behaviour in dilute solutions. Industrial Crops and Products. Mar. 2008;27(2):214-19.

(Continued)

*Primary Examiner* — Kevin E Weddington
(74) *Attorney, Agent, or Firm* — Oyen Wiggs Green & Mutala LLP

(57) ABSTRACT

The use of a composition which comprises lignosulfonate and is substantially free of elemental sulphur for the prevention and treatment of pathogenic and medical disorders in humans and animals. In some embodiments the lignosulfonate is radically polymerized. In some embodiments the composition is formulated as an animal feed additive or supplement. The disclosure also encompasses a method of preventing or treating a pathogenic or medical disorder in a human or animal subject by administering the composition to the subject in an effective dose to attenuate the pathogenic effect of a pathogen or other biological agent, thereby enabling the subject to mount an effective immune response to the pathogen or other biological agent. The composition can be used in the prevention or treatment of a wide range of pathogenic or medical disorders including disorders caused by microbial pathogens; disorders caused by viral pathogens; disorders caused by prions; disorders caused by protists; disorders caused by fungi; disorders caused by parasites; lung and airway disorders; bone, joint and muscle disorders; digestive disorders; hormonal disorders; cancer; auto immune disorders; neurodegenerative disorders; skin disorders; and sexual and reproductive disorders. In one particular embodiment the composition is formulated for treatment of Type I diabetes.

9 Claims, 3 Drawing Sheets

(56) References Cited

OTHER PUBLICATIONS

Reddy BS, Maeura Y, Wayman M. Effect of dietary corn bran and autohydrolyzed lignin on 3,2'-dimethyl-4-aminobiphenyl-induced intestinal carcinogenesis in male F344 rats. J Natl Cancer Inst. Aug. 1983;71(2):419-23.

Rajadurai M, Prince PSM. Preventive effect of naringin on isoproterenol-induced cardiotoxicity in Wistar rats: an in vivo and in vitro study. Toxicology. Apr. 11, 2007;232(3):216-25.

Thompson JL, Mallet-Boucher M, McCloskey C, Tamlyn K, Wilson K. Educating nurses for the twenty-first century abilities-based outcomes and assessing student learning in the context of democratic professionalism. Int J Nurs Educ Scholarsh. Oct. 9, 2013;10.

Ryden A, Stechova K, Durilova M, Faresjö M. Switch from a dominant Th1-associated immune profile during the pre-diabetic phase in favour of a temporary increase of a Th3-associated and inflammatory immune profile at the onset of type 1 diabetes. Diabetes Metab Res Rev. May 2009;25(4):335-43.

Hyöty H, Hiltunen M, Knip M, Laakkonen M, Vähäsalo P, Karjalainen J, et al. A prospective study of the role of coxsackie B and other enterovirus infections in the pathogenesis of IDDM. Childhood Diabetes in Finland (DiMe) Study Group. Diabetes. Jun. 1995;44(6):652-7.

Elfaitouri A, Berg AK, Frisk G, Yin H, Tuvemo T, Blomberg J. Recent enterovirus infection in type 1 diabetes: evidence with a novel IgM method. J Med Virol. Dec. 2007;79(12):1861-7.

Palmer JP, Asplin CM, Clemons P, Lyen K, Tatpati O, Raghu PK, et al. Insulin antibodies in insulin-dependent diabetics before insulin treatment. Science. Dec. 23, 1983;222(4630):1337-9.

Rich SS. Mapping genes in diabetes. Genetic epidemiological perspective. Diabetes. Nov. 1990;39(11):1315-9.

Tuomilehto J, Podar T, Tuomilehto-Wolf E, Virtala E. Evidence for importance of gender and birth cohort for risk of IDDM in offspring of IDDM parents. Diabetologia. Aug. 1995;38(8):975-82.

Bottazzo GF, Florin-Christensen A, Doniach D. Islet-cell antibodies in diabetes mellitus with autoimmune polyendocrine deficiencies. Lancet. Nov. 30, 1974;2(7892):1279-83.

Orban T, Sosenko JM, Cuthbertson D, Krischer JP, Skyler JS, Jackson R, et al. Pancreatic islet autoantibodies as predictors of type 1 diabetes in the Diabetes Prevention Trial-Type 1. Diabetes Care. Dec. 2009;32(12):2269-74.

Soberanes S, Misharin A v, Jairaman A, Morales-Nebreda L, McQuattie-Pimentel AC, Cho T, et al. Metformin Targets Mitochondrial Electron Transport to Reduce Air-Pollution-Induced Thrombosis. Cell Metab. 2019;29(2):335-347.e5.

Arif S, Leete P, Nguyen V, Marks K, Nor NM, Estorninho M, et al. Blood and islet phenotypes indicate immunological heterogeneity in type 1 diabetes. Diabetes. Nov. 2014;63(11):3835-45.

Kefas BA, Cai Y, Kerckhofs K, Ling Z, Martens G, Heimberg H, et al. Metformin-induced stimulation of AMP-activated protein kinase in beta-cells impairs their glucose responsiveness and can lead to apoptosis. Biochem Pharmacol. Aug. 1, 2004;68(3):409-16.

Corkey BE. Banting lecture 2011: hyperinsulinemia: cause or consequence? Diabetes. Jan. 2012;61(1):4-13.

Czech MP. Insulin action and resistance in obesity and type 2 diabetes. Nat Med. Jul. 11, 2017;23(7):804-14.

Jędrzejczak P, Collins MN, Jesionowski T, Klapiszewski Ł. The role of lignin and lignin-based materials in sustainable construction—A comprehensive review. Int J Biol Macromol. Sep. 30, 2021;187:624-50.

Akkati S, Sam KG, Tungha G. Emergence of promising therapies in diabetes mellitus. J Clin Pharmacol. Jun. 2011;51(6):796-804.

Reddy VD, Padmavathi P, Paramahamsa M, Varadacharyulu NC. Amelioration of alcohol-induced oxidative stress by Emblica officinalis (amla) in rats. Indian J Biochem Biophys. Feb. 2010;47(1):20-5.

de Sousa E, Zanatta L, Seifriz I, Creczynski-Pasa TB, Pizzolatti MG, Szpoganicz B, et al. Hypoglycemic effect and antioxidant potential of kaempferol-3,7-O-(alpha)-dirhamnoside from Bauhinia forficata leaves. J Nat Prod. May 2004;67(5):829-32.

Bailey CJ. Metformin: historical overview. Diabetologia. 2017;60(9):1566-76.

Eisenbarth GS. Update in type 1 diabetes. J Clin Endocrinol Metab. Jul. 2007;92(7):2403-7.

Eisenbarth GS, Jeffrey J. The natural history of type 1A diabetes. Arq Bras Endocrinol Metabol. Mar. 2008;52(2):146-55.

Rena G, Hardie DG, Pearson ER. The mechanisms of action of metformin. Diabetologia. 2017;60(9):1577-85.

Erion KA, Corkey BE. Hyperinsulinemia: a Cause of Obesity?. Curr Obes Rep. 2017;6:178-186.

Page MM, Johnson JD. Mild Suppression of Hyperinsulinemia to Treat Obesity and Insulin Resistance. Trends in Endocrinology & Metabolism. 2018;29(6):389-399.

Ye J. Role of insulin in the pathogenesis of free fatty acid-induced insulin resistance in skeletal muscle. Endocr Metab Immune Disord Drug Targets. Mar. 2007;7(1):65-74.

Hedman M, Ludvigsson J, Faresjö MK. Nicotinamide reduces high secretion of IFN-gamma in high-risk relatives even though it does not prevent type 1 diabetes. J Interferon Cytokine Res. Apr. 2006;26(4):207-13.

Proportions of NOD mice that became diabetic in the prevention of diabetes onset study. Mice treated with TemStik and Composition 3 - Low had diabetes onset at 15 weeks of age, whereas mice in all other groups became diabetic between 11-13 weeks of age. Comparison between treated groups vs. saline-treated control group was performed.

A. First Experiment

B. Second Experiment

C. Pooled Results of First and Second Experiments

A. First Experiment

B. Second Experiment

C. Pooled Results of First and Second Experiments

METHOD AND USE OF COMPOSITIONS COMPRISING LIGNOSULFONATE AND SUBSTANTIALLY FREE OF ELEMENTAL SULPHUR FOR PATHOGENIC ATTENUATION

RELATED APPLICATIONS

This application claims the benefit of US provisional patent application No. 62/703,755 filed 26 Jul. 2018, which is hereby incorporated by reference in its entirety.

TECHNICAL FIELD

This application relates to the use of compositions comprising lignosulfonate and substantially free of elemental sulphur for prevention and treatment of pathogenic and medical disorders in humans and animals.

BACKGROUND

Many medical disorders are caused by pathogenic agents such as bacteria or viruses. Conventional treatment of such disorders is focused on killing or removing the pathogen, such as by administering antibiotics or anti-viral drugs. However, such treatment is often not effective. For example, bacteria tend to develop resistance to antibiotics over time, requiring the development of new drugs or drug combinations or other therapies.

Compositions intended to attenuate the effect of pathogenic agents are known in the prior art. For example, United States Patent Application Publication No. US 2015/0132390 A1, which is hereby incorporated by reference in its entirety, describes a pharmaceutical preparation comprising as an active ingredient micron-sized sulphur particles. The preparation may also include sodium lignin sulphate (sometimes referred to as sodium lignosulfonate). As described in the '390 publication, the purpose of the sulphur particles is not to kill a target pathogen but rather to re-establish a healthy equilibrium or homeostasis from a pathological imbalance or disorder. According to the theory of the '390 disclosure, the compound is believed to act by depriving the pathogen of oxygen with available sulphur atoms that are oxidized. This results in a "pathogenic attenuation", namely a slowing down or decrease in the rate of reproduction of the pathogen. Such attenuation enables the host's natural defences, such as the host's immune system, to more quickly and effectively eliminate or control the pathogen. Moreover, attenuation of pathogens may result in less prolonged activation of the host's defences which may improve the overall health and physiological performance of the animal.

Patents and patent applications related to the '390 publication have been granted and/or published as follows: AU20072572862; CA265408C; CN101500584B; EP2035018B1; JP2009538837A; JP2013231072A; KR10146209B1; MX2008015200A; and NZ597657. All of the above patents and publications are hereby incorporated by reference in their entirety.

The '390 publication and related patents and/or publications identify elemental sulphur as the active therapeutic ingredient. Sodium lignin sulphonate is described as acting as a catalyst for removing the sulphur atoms from a ring structure thereby making the sulphur atoms available for systemic oxidization and a corresponding reduction in the production of systemic hydrogen protons. However, the inventor of the present disclosure has determined that compositions comprising lignosulfonate are biologically effective for use in pathogenic attenuation even in the absence of elemental sulphur. The present disclosure is therefore directed to compositions which comprise lignosulfonate and are substantially free of elemental sulphur.

The foregoing examples of the related art and limitations related thereto are intended to be illustrative and not exclusive. Other limitations of the related art will become apparent to those of skill in the art upon a reading of the specification and a study of the drawing(s).

SUMMARY

The following embodiments and aspects thereof are described and illustrated in conjunction with systems, tools and methods which are meant to be exemplary and illustrative, not limiting in scope. In various embodiments, one or more of the above-described problems have been reduced or eliminated, while other embodiments are directed to other improvements.

In one aspect, this application relates to the use of a composition comprising lignosulfonate for the prevention and treatment of pathogenic and medical disorders in humans and animals, wherein said composition is substantially free of elemental sulphur. In one particular aspect the composition comprises radically polymerized sodium lignosulfonate.

In another aspect, this application relates to a method of preventing or treating a pathogenic or medical disorder in a human or animal subject comprising administering to the subject an effective amount of a composition comprising lignosulfonate, wherein the composition is substantially free of elemental sulphur.

In another aspect, this application relates to a pharmaceutical composition comprising lignosulfonate, wherein the composition is substantially free of elemental sulphur and is formulated in a dosage for use in the prevention or treatment of a pathogenic or medical disorder in a human or animal subject.

In addition to the exemplary aspects and embodiments described above, further aspects and embodiments will become apparent by reference to the drawings and by study of the following detailed descriptions.

BRIEF DESCRIPTION OF THE DRAWINGS

Exemplary embodiments are illustrated in referenced figures of the drawing(s). It is intended that the embodiments and figure(s) disclosed herein are to be considered illustrative rather than restrictive.

FIG. 2A shows results from a first experiment. FIG. 2B shows results from a second experiment. FIG. 2C shows pooled results from the first and second experiments.

FIG. 3A shows results from a first experiment. FIG. 3B shows results from a second experiment. FIG. 3C shows pooled results from the first and second experiments. ATP levels were measured using an ATP assay kit.

DESCRIPTION

Figure 1:
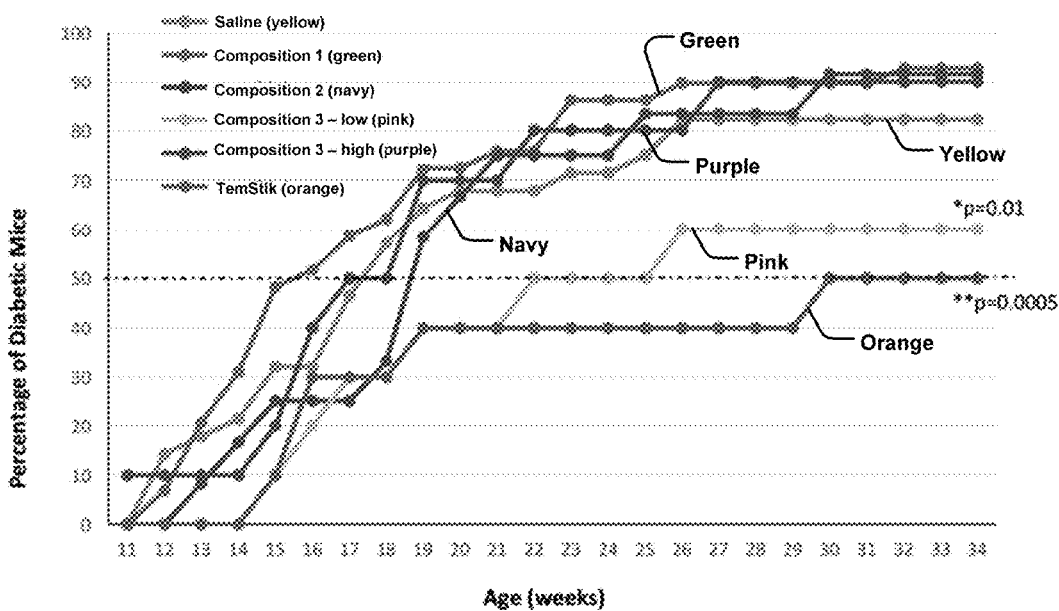
FIG. 1 is a graph showing proportions of NOD mice that became diabetic when administered with compositions comprising lignosulfonate and variable amounts of elemental sulphur (or no elemental sulphur).

Throughout the following description specific details are set forth in order to provide a more thorough understanding to persons skilled in the art. However, well known elements may not have been shown or described in detail to avoid unnecessarily obscuring the disclosure. Accordingly, the description and drawings are to be regarded in an illustrative, rather than a restrictive, sense.

This application relates to the use of a composition comprising lignosulfonate for the prevention and treatment of pathogenic and medical disorders in humans and animals, wherein the composition is substantially free of elemental sulphur. Along with cellulose, lignin is one of the primary constituents providing the structure of wood. Lignosulfonates are amorphous branched polymers of lignin resulting from the sulfite pulping process used to delignify wood or other lignocellulosic biomasses. Lignosulfonates may contain sulfonated covalently linked phenyl propane monomers and other heterogeneous compounds.

Lignosulfonates are commonly used for many different applications, including as binders, pelletizing agents, briquetting agents, anti-caking agents, surfactants, dust suppressants and coagulants. Lignosulfonates are also used as macronutrients in feedingstuffs for animals, including cattle, pigs and chickens. Toxicological studies on lignosulfonates indicate that they are non-toxic. In the literature, the LD50 for lignosulfonates has been reported to be 20,000 mg/kg body weight be ingestion. Materials with LD50 values of 5,000 mg/kg of body weight or greater are considered to be non-toxic (e.g. Material Safety Data Sheet, Ammonium lignosulfonate liquid, Tembec—Chemical Group, accessible online at www.maritimehydroseed.com/images/TDS_MSD-S.pdt). Further, lignosulfonates have been approved by the USDA for inclusion in animal feeds.

The inventor of the present disclosure has determined that compositions comprising lignosulfonates when administered in a biological effective dose are useful in the prevention and/or treatment of pathogenic or medical disorders in animals. In some embodiments the lignosulfonates may be radically polymerized. For example, the lignosulfonates may be radically polymerized by subjecting the lignosulfonates to very high heat. This biological effect occurs even in the absence of elemental sulphur in the administered compositions. Without being bound by any particular theory, the inventor believes that the compositions are acting by attenuation of pathogens or other biological agents, enabling the host animal to mount an effective immune or other biological response. For example, the compositions may prevent the pathogen population from growing exponentially in the host animal, thereby enabling the animal to mount an effective immune or other biological response.

As used in this patent application "pathogenic and medical disorders" refers to disorders caused by pathogens or other causes. Pathogenic disorders include disorders caused by pathogens such as bacteria, viruses, prions, protists, fungi and parasitic worms. Medical disorders include disorders resulting in abnormal biological functioning caused by non-pathogens, or only partially caused by pathogens, such as cancer, diabetes mellitus, and reproductive maladies. One particular type of medical disorder is dementia, including Alzheimer's disease. By way of further example, pathogenic and medical disorders may include disorders caused by microbial pathogens; disorders caused by viral pathogens; disorders caused by prions; disorders caused by protists; disorders caused by fungi; disorders caused by parasites; lung and airway disorders; bone, joint and muscle disorders; digestive disorders; hormonal disorders; cancer; auto immune disorders; neurodegenerative disorders; skin disorders; and sexual and reproductive disorders.

Compositions comprising lignosulfonates are generally available from a wide variety of sources. By way of an exemplary example, a composition comprising radically polymerized sodium lignosulfonates is or has been available from the Tembec—Chemical Group, acquired by Rayonier Advanced Materials, and has been sold under the trademark ARBO®TemStik (hereinafter "TemStik"). A chemical analysis of TemStik in powder form has confirmed that it does not include a measurable amount of elemental sulphur. In particular, the TemStik composition contained less than the reportable detection limit of sulphur (elemental) in a chemoanalytic analysis where the detection limit was 100 mg/kg.

The TemStik composition comprising radically polymerized lignosulfonates may also comprise measurable amounts of tannic acid and aldehydes such as formaldehyde, acetaldehyde and propionaldehyde. Without being bound by any particular theory, the inventor believes that one or more of the above constituents could provide a biological effect in vivo, either directly or acting synergistically with other multi-molecular constituents. Further, without being bound by any particular theory, the inventor believes that the TemStik composition comprising radically polymerized lignosulfonates may function as an ATP inhibitor to effect broad-spectrum pathogenic attenuation at biologically effective dosages.

Example 1—Administration of TemStik to Livestock

A supply of TemStik in powder format was purchased in 25 kg bags. Two bags of TemStik, namely 50 kg, was mixed with 4 metric tons, namely 4,000 kg, of animal feed. This ratio corresponds to 12.5 g of TemStik per kg of feed. The animal feed comprised 2000 kg of barley, 1000 kg of wheat and 1000 kg of peas. The animal feed supplemented with TemStik was fed to livestock, principally swine. In this example 100 swine each weighing on average 50 kg were fed 4 metric tons of animal feed over 4 days in a livestock pen. Thus each swine consumed on average 10 kg of animal feed comprising 125 g of TemStik per day. That is, for every 50 kg of animal weight, approximately 125 g of TemStik was administered per day. This corresponds to a daily dosage of 2.5 g of TemStik per kg of livestock weight. Based on experience administering feed supplements to livestock, the inventor believes that minimum and maximum daily dosage may vary significantly from the dosage provided in this example while maintaining biological efficacy. For example, in some embodiments the minimum and maximum daily dosage may vary by 20% from the dosage provided in this example. Thus in such embodiments the daily dosage of TemStik per kg of livestock weight could vary within the range of approximately 2-3 g of TemStik per kg of livestock weight. In another embodiment the daily dosage of TemStik per kg of livestock weight could be reduced by approximately 50% from the dosage provided in this example while maintaining biological efficacy.

The livestock was monitored over an extended period of time and exhibited excellent health without the need to administer prophylactic or therapeutic antibiotics or other veterinary drugs. In particular, the livestock exhibited excellent viability, resistance to pathogenic and medical disorders, and excellent reproductive performance. For example, although the livestock were not administered with any vaccines, anti-microbial agents or other anti-parasitic agents, and were subject to periodic inspection by Canadian federal government regulators, very few animals or animal organs were condemned due to parasitic or other animal diseases. The number of swine slaughtered and subject to inspection per year was approximately 5,000.

Example 2—Use to TemStik in Mice to Inhibit the Onset of Type I Diabetes

The biological efficacy of TemStik was investigated in an animal model of Type I diabetes using non-obese diabetic (NOD) mice. In this example TemStik was compared to other compositions comprising both lignosulfonates and elemental sulphur in varying proportions as well as to a saline control. The mice were five-week old female NOD mice. One intraperitoneal injection of TemStik at 5 mg/ml was administered to NOD mice on the first day of the experiment followed by a second injection one day later. On the second day of the experiment TemStik was provided to the mice in their drinking water at a concentration of 1 mg/ml. The other test compositions (Compositions 1-3) and saline control were administered in a similar manner, except that Composition 3 was provided to mice in their drinking water at concentrations of 0.04 mg/ml (Low) or 0.2 mg/ml (High).

The proportion of NOD mice that became diabetic in this example is graphically illustrated in FIG. 1. In the case of the mice administered with TemStik, 5 of the 10 mice treated remained non-diabetic after 30 weeks of treatment. The time of diabetes onset in weeks for individual mice administered with TemStik was as follows: 15, 16(×2), 19, 30, 34 and 35(×4). This corresponds to Mean±SEM (weeks) of 27.00±2.91. This experimental data demonstrates that TemStik was significantly more effective in preventing the onset of diabetes than the other tested compositions and the saline control. The test composition that was the next most effective in preventing the onset of diabetes was the composition containing lignosulfonate but having the smallest concentration of elemental sulphur (Composition 3—Low). This experiment demonstrates that compositions comprising lignosulfonate but substantially free of elemental sulphur are effective in preventing the onset of Type I diabetes.

Example 3—ATP Inhibition

As indicated above, it is believed the TemStik composition comprising radically polymerized lignosulfonates may function as an ATP inhibitor, likely via ATPase enzymes embedded in the mitochondrial membrane, to effect broad-spectrum pathogenic attenuation at biologically effective dosages.

Figure 2A:
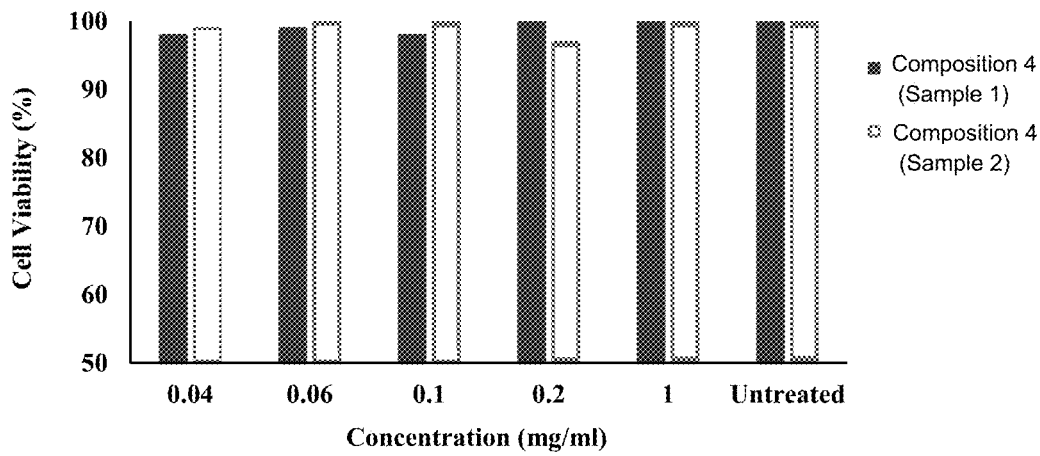
FIGS. 2A-2C are graphs showing the effect of various concentrations of TemStik (identified as Composition 4) on the viability of a mouse beta cell line. Cell viability of mouse beta cells was determined by Trypan blue exclusion dye. Mouse beta cells were seeded at $3 \times 10^6$ cells per well and treated with different concentrations of Composition 4 and incubated for 24 hours under standard culture conditions.
Figure 2B:
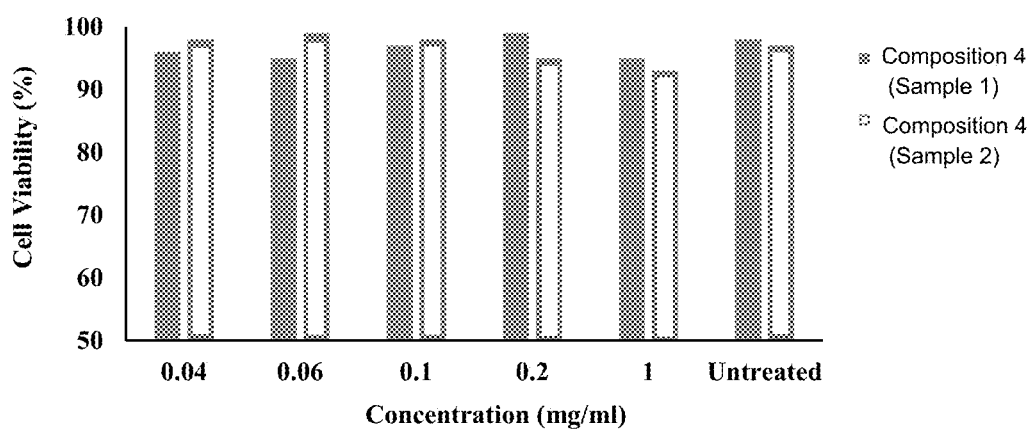
Figure 2C:
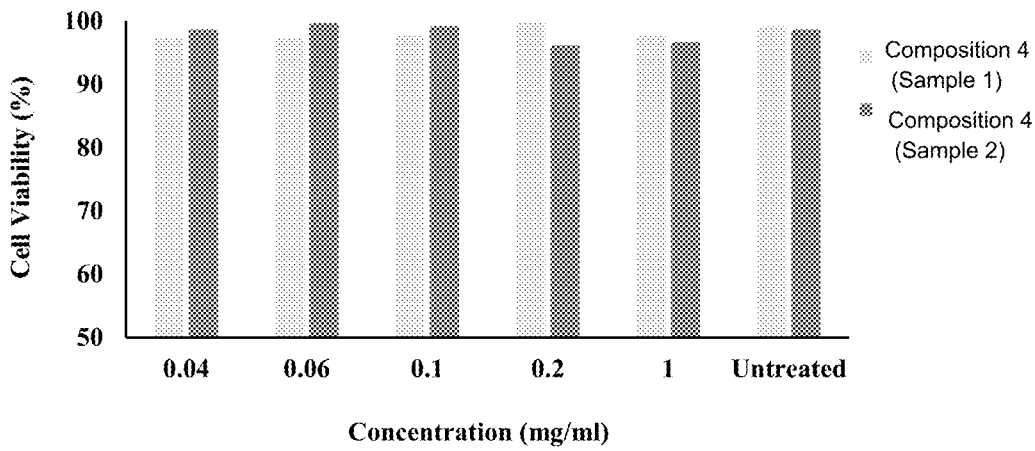

FIGS. 2A-2C show the effect of various concentrations of TemStik (Composition 4) on the viability of a mouse beta cell line. Two different samples of Composition 4 were tested. Regardless of the sample source and dose of Composition 4, the viability of the beta cells treated with Composition 4 remained high and comparable to those observed in untreated cells.

Figure 3A:
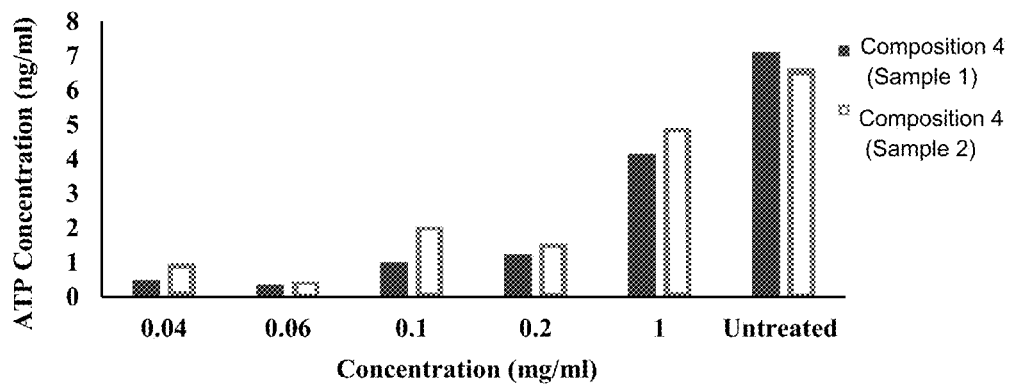
FIGS. 3A-3C are graphs showing ATP concentration in mouse beta cells as measured by colorimetric assay. Mouse beta cells were seeded at $3 \times 10^6$ cells per well and treated with different concentrations of Composition 4 and incubated for 24 hours under standard culture conditions.
Figure 3B:
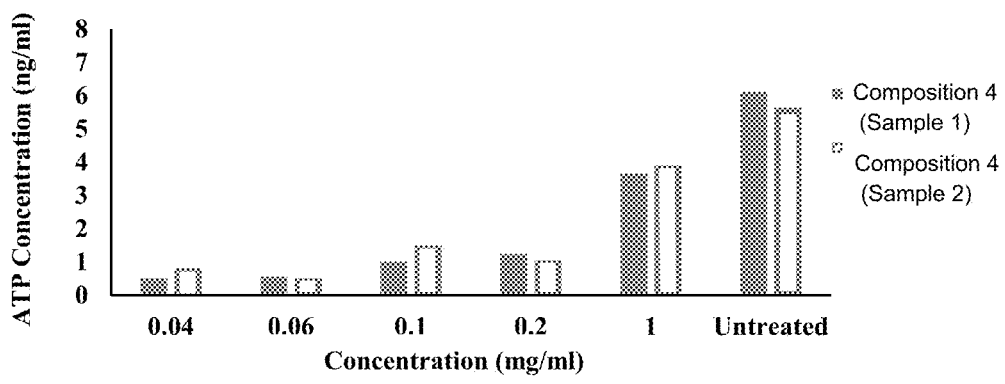
Figure 3C:
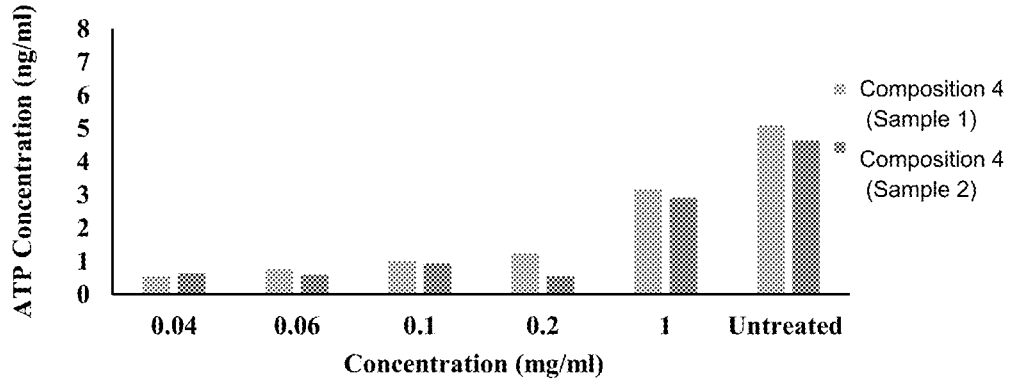

FIGS. 3A-3C show the effect of various concentrations of Composition 4 on ATP concentration in mouse beta cells. The level of ATP concentration in cells treated with Composition 4 are significantly lower compared to those detected in untreated cells. ATP levels were measured using an ATP assay kit.

Example 4—Swine Serological Study

A serological study of swine fed with animal feed supplemented with TemStik was conducted. The daily dosage of TemStik per kg of livestock weight was approximately 50% of the dosage described in Example 1 above. Blood samples from 30 individual animals was collected and analyzed. The analysis showed that the swine tested positive for antibodies to various pathogenic agents. The detected antibodies included influenza H3N2 antibody; *Mycoplasma hyopneumoniae* antibody; and influenza H1 antibody. The following antibodies were not detected above the detection limit: PRRSV antibody and TGEV-PRCV antibody. The absence of the undetected antibodies was somewhat surprising since such antibodies were present in earlier tests of the swine herd, e.g. ancestor animals.

The swine cohort in question were not administered with any vaccines, anti-microbial agents, anti-parasitic agents or other veterinary drugs. Despite the presence of antibodies suggesting exposure to various pathogenic agents, the swine cohort exhibited excellent viability, resistance to pathogenic and medical disorders, and excellent reproductive performance. Further, following slaughter of the swine, very few animals or animal organs were condemned.

Example 5

Wild boar fed with animal feed supplemented with TemStik were slaughtered in a Canadian Food Inspection Agency (CFIA) regulated plant in Manitoba, Canada. The daily dosage of TemStik per kg of livestock weight was approximately 50% of the dosage described in Example 1 above. The wild boar in question were not administered with any vaccines, anti-microbial agents, anti-parasitic agents or other veterinary drugs. In the Manitoba plant a total of 2,783 head of wild boar were slaughtered over a period of several months and only 19 (0.7%) of the slaughtered animals were condemned.

Wild boar fed with animal feed supplemented with TemStik were slaughtered in a Canadian Food Inspection Agency (CFIA) regulated plant in Quebec, Canada. The daily dosage of TemStik per kg of livestock weight was approximately 50% of the dosage described in Example 1 above. The wild boar in question were not administered with any vaccines, anti-microbial agents, anti-parasitic agents or other veterinary drugs. In the Quebec plant a total of 800 head of wild boar were slaughtered over a period of several months and none of the slaughtered animals were condemned.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are consistent with the broadest interpretation of the specification as a whole.

The invention claimed is:

1. A method of preventing or treating a pathogenic or medical disorder in a human or animal subject in need thereof comprising administering to said subject an effective amount of a composition comprising lignosulfonate, wherein said composition is substantially free of elemental sulphur, and wherein said pathogenic or medical disorder is Type I diabetes mellitus.

2. The method as defined in claim 1, wherein said lignosulfonate is radically polymerized lignosulfonate.

3. The method as defined in claim 1, wherein said composition comprises lignosulfonate selected from the group of ammonium lignosulfonate, sodium lignosulfonate, calcium lignosulfonate and magnesium lignosulfonate.

4. The method as defined in claim 1, wherein said composition is formulated for administration as an animal feed additive.

5. The method as defined in claim 4, wherein said composition is administered at a daily dosage of 2-3 g per kg weight of said animal.

6. The method as defined in claim 5, wherein said daily dosage is 2.5 g per kg weight of animal.

7. The method as defined in claim 1, wherein said administration is by oral administration.

8. The method as defined in claim 1, wherein said administration is by intraperitoneal injection.

9. A method of treating a pathogenic or medical disorder in a human or animal subject in need thereof comprising administering to said subject an effective amount of a composition comprising lignosulfonate, wherein said composition is substantially free of elemental sulphur, and wherein said pathogenic or medical disorder is Type I diabetes mellitus.

* * * * *